US012005175B2

United States Patent
Furuhashi et al.

(10) Patent No.: US 12,005,175 B2
(45) Date of Patent: Jun. 11, 2024

(54) BLOOD PURIFICATION DEVICE

(71) Applicant: Nikkiso Company Limited, Tokyo (JP)

(72) Inventors: Tomohiro Furuhashi, Shizuoka (JP); Kazuhide Ono, Shizuoka (JP); Hideto Maki, Shizuoka (JP); Ferenc Kazinczi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 456 days.

(21) Appl. No.: 17/417,670

(22) PCT Filed: Aug. 29, 2019

(86) PCT No.: PCT/JP2019/033855
§ 371 (c)(1),
(2) Date: Jun. 23, 2021

(87) PCT Pub. No.: WO2020/136998
PCT Pub. Date: Jul. 2, 2020

(65) Prior Publication Data
US 2022/0111134 A1 Apr. 14, 2022

(30) Foreign Application Priority Data
Dec. 28, 2018 (JP) .................................. 2018-248123

(51) Int. Cl.
*A61M 1/36* (2006.01)
(52) U.S. Cl.
CPC ........ *A61M 1/3644* (2014.02); *A61M 1/3607* (2014.02); *A61M 1/3624* (2013.01);
(Continued)
(58) Field of Classification Search
CPC .............. A61M 1/3644; A61M 1/3607; A61M 1/3624; A61M 1/3623; A61M 2205/18;
(Continued)

(56) References Cited

U.S. PATENT DOCUMENTS

2012/0061320 A1* 3/2012 Nuernberger ......... A61M 1/342
210/103

FOREIGN PATENT DOCUMENTS

CN 103826672 A 5/2014
CN 108348671 A 7/2018
(Continued)

OTHER PUBLICATIONS

Japanese Office Action for Application No. 2018-248123, dated Sep.6, 2022, with English translation, 6 pages.
(Continued)

*Primary Examiner* — Krishnan S Menon
(74) *Attorney, Agent, or Firm* — Young Basile Hanlon & MacFarlane, P.C.

(57) ABSTRACT

A blood purification device includes a blood circuit for extracorporeally circulating blood of a patient; a liquid supply circuit for supplying a supply liquid to the blood circuit or to a blood purifier provided on the blood circuit and a waste liquid circuit for discharging the waste liquid from the blood purifier. Each of the blood circuit, the liquid supply circuit and the waste liquid circuit comprises a flexible tube. The blood purification device comprises a tube identification unit that performs a tube identification process for identifying a tube used for the blood circuit, the liquid supply circuit or the waste liquid circuit or determining whether or not there is an abnormality in the tube, based on an amount of liquid sent from a peristaltic pump provided on the blood circuit, the liquid supply circuit or the waste liquid circuit, or pressure fluctuation in the circuit, caused when driving the pump for a predetermined time.

8 Claims, 3 Drawing Sheets

(52) U.S. Cl.
CPC ....... *A61M 1/3623* (2022.05); *A61M 2205/18* (2013.01); *A61M 2205/3393* (2013.01); *A61M 2205/502* (2013.01)

(58) Field of Classification Search
CPC .... A61M 2205/3393; A61M 2205/502; A61M 1/367; A61M 2205/60; A61M 1/1643
See application file for complete search history.

(56) References Cited

FOREIGN PATENT DOCUMENTS

| EP | 3369442 A1 | 9/2018 |
|---|---|---|
| JP | S62004346 B2 | 1/1987 |
| JP | 2013-052229 A | 3/2013 |
| JP | 2017-080266 A | 5/2017 |
| WO | 2013/022024 A1 | 2/2013 |

OTHER PUBLICATIONS

International Search Report for Application No. PCT/JP2019/033855, dated Nov. 12, 2019.
European Search Report for Application No. 19905739.9, dated Aug. 26, 2022, 7 pgs.
Chinese Office Action for Application No. 201980085954.8, dated Nov. 23, 2023, with English translation, 16 pgs.

\* cited by examiner

BLOOD PURIFICATION DEVICE

CROSS-REFERENCE TO RELATED APPLICATION(S)

This application is a national stage entry of International Application No. PCT/JP2019/033855, filed on Aug. 29, 2019, which claims priority to Japanese Application No. 2018-248123, filed on Dec. 28, 2018, the entire disclosures of which are hereby incorporated by reference.

TECHNICAL FIELD

The invention relates to a blood purification device.

BACKGROUND ART

A blood purification device in which plural types of tubes with different inner diameters and different priming volumes (PVs) are applicable as a blood circuit, etc., is known. It is common practice to properly use, e.g., a standard PV circuit tube for adults and a low PV circuit tube for light-weight patients such as newborn babies, according to the body weight, etc., of the patient.

Patent Document 1 can be found as prior art document information related to the invention of the present application.

CITATION LIST

Patent Literature

Patent Document 1: JP2017/80266A

SUMMARY OF INVENTION

Technical Problem

In general, specific control details such as a target flow rate range during treatment are different between when using a standard PV circuit for adult patients and when using a low PV circuit for light-weight patients such as newborn babies. Therefore, an unintended flow rate control may be performed if the priming volume of the tube in the control setting is different from the priming volume of the actually attached tube. An unintended flow rate control may be performed also when there is abnormality in the tube.

Therefore, it is an object of the invention to provide a blood purification device capable of identifying an attached tube or detecting an abnormality in the tube.

Solution to Problem

The invention according to variation 1 is a blood purification device, comprising: a blood circuit for extracorporeally circulating blood of a patient; a liquid supply circuit for supplying a supply liquid to the blood circuit or to a blood purifier provided on the blood circuit; and a waste liquid circuit for discharging a waste liquid from the blood purifier, wherein each of the blood circuit, the liquid supply circuit and the waste liquid circuit comprises a flexible tube, and the device comprises a tube identification unit that performs a tube identification process for identifying a tube used for the blood circuit, the liquid supply circuit or the waste liquid circuit or determining whether or not there is an abnormality in the tube, based on an amount of liquid sent from a peristaltic pump provided on the blood circuit, the liquid supply circuit or the waste liquid circuit, or pressure fluctuation in the circuit, caused when driving the pump for a predetermined time.

The invention according to variation 2 is the blood purification device according to variation 1, comprising: a removed water amount detection unit for detecting an amount of removed water based on a supplied amount of the supply liquid and a discharged amount of the waste liquid, wherein the removed water amount detection unit comprises a supply liquid subdivision chamber being provided on the liquid supply circuit and temporarily storing the supply liquid, a waste liquid subdivision chamber being provided on the waste liquid circuit and temporarily storing the waste liquid, and a weight detection mechanism for detecting a total weight of the supply liquid subdivision chamber and the waste liquid subdivision chamber, and the tube identification unit uses the weight detection mechanism of the removed water amount detection unit and detects the amount of liquid sent from the pump provided on the liquid supply circuit or the waste liquid circuit when driving the pump for a predetermined time.

The invention according to variation 3 is the blood purification device according to variation 1, wherein the tube identification unit performs the tube identification process during when priming each circuit with a liquid before blood purification treatment.

The invention according to variation 4 is the blood purification device according to variation 1, comprising: an alarm unit that issues an alarm when a tube actually used for each circuit and identified by the tube identification unit does not match a tube of each circuit in a preset setting.

The invention according to variation 5 is the blood purification device according to variation 4, comprising: a display for displaying a predetermined screen, wherein the alarm unit issues an alarm by displaying an alarm screen corresponding to the details of the alarm on the display.

The invention according to variation 6 is the blood purification device according to variation 5, wherein a setting change reception part for receiving an operation to change a preset tube setting is displayed on the alarm screen.

The invention according to variation 7 is the blood purification device according to variation 1, wherein the tube identification unit is configured to be able to determine whether or not there is an abnormality in the tube in use, based on whether or not the amount of liquid sent from the pump or the pressure fluctuation when driving the pump for a predetermined time falls within a preset normal range.

The invention according to variation 8 is the blood purification device according to variation 1, comprising: a pump speed correction unit that corrects a pump speed of the pump driven at the time of the measurement, based on a measurement result of the amount of liquid sent from the pump or the pressure fluctuation during the tube identification process.

Advantageous Effects of Invention

According to the invention in variation 1, it is possible to provide a blood purification device capable of identifying an attached tube or detecting an abnormality in the tube.

According to the invention in variation 2, by using the removed water amount detection mechanism also for identification, it is possible to identify the circuit at low cost without additionally providing a sensor.

According to the invention in variation 3, since appropriateness/inappropriateness of the circuit can be determined before beginning treatment, it is possible to prevent treatment using an inappropriate circuit.

According to the invention in variation 4, it is possible to encourage users to take an appropriate action by issuing an alarm.

According to the invention in variation 5, the users can easily know the details of the alarm, hence, convenience is improved.

According to the invention in variation 6, in case that the tube setting is incorrect, the setting can be changed directly on the alarm screen without inputting the setting details all over again, hence, convenience is improved.

According to the invention in variation 7, since it is possible to determine whether or not there is an abnormality in the circuit, use of the abnormal circuit can be suppressed after the determination.

According to the invention in variation 8, it is possible to send the liquid at an appropriate pump speed and it is also possible to perform tube identification as well as pump speed correction using a common measurement result (the amount of liquid sent from the pump or the pressure fluctuation).

DESCRIPTION OF EMBODIMENT

Embodiment

An embodiment of the invention will be described below in conjunction with the appended drawings.

Figure 1:
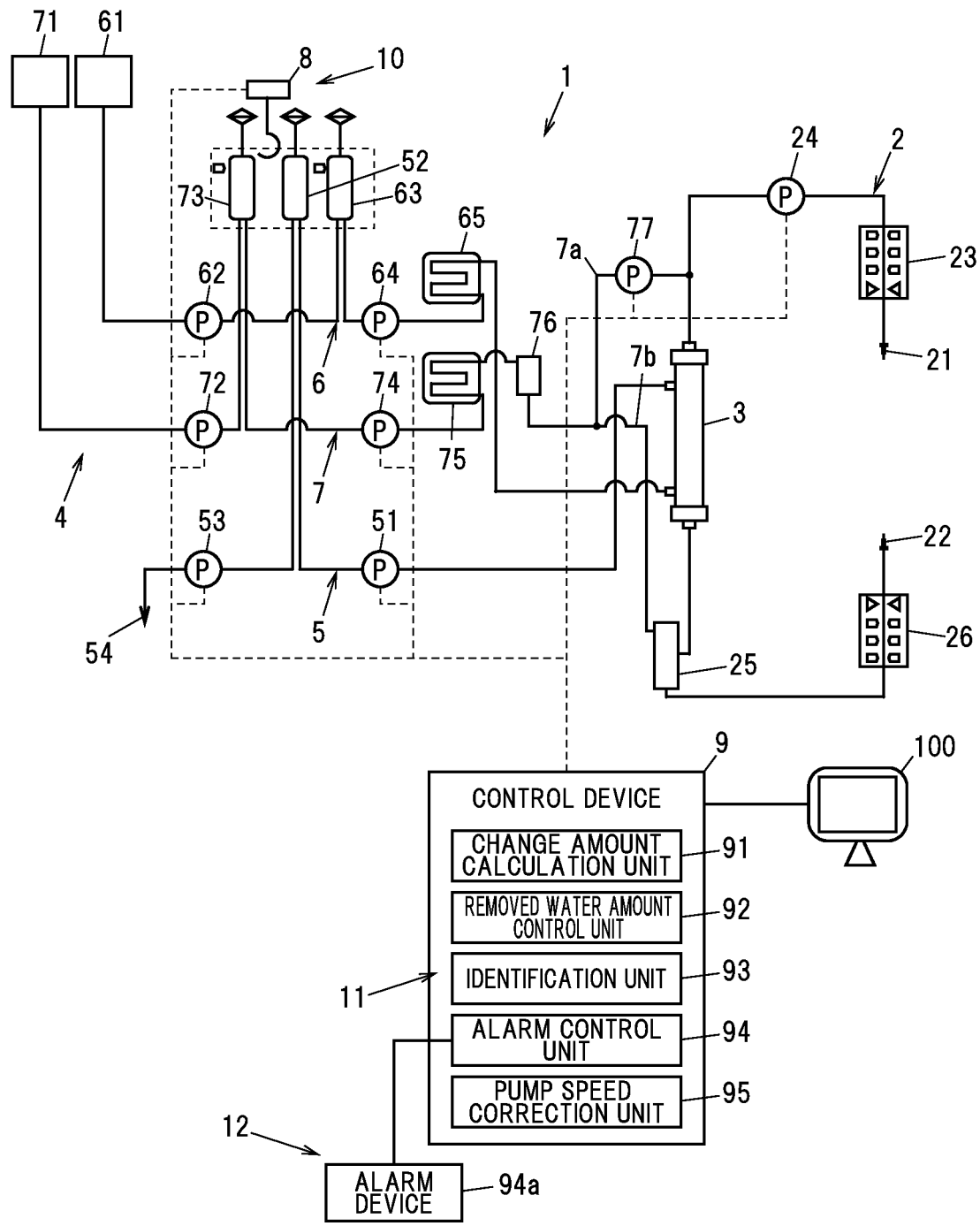
FIG. 1 is a schematic configuration diagram illustrating a blood purification device in an embodiment of the present invention.

FIG. 1 is a schematic configuration diagram illustrating a blood purification device in the present embodiment. As shown in FIG. 1, a blood purification device 1 includes a blood circuit 2 for extracorporeally circulating blood of a patient, a blood purifier 3 being provided on the blood circuit 2 and purifying the blood, liquid supply circuits 4 for supplying supply liquids to the blood purifier 3 or the blood circuit 2, and a waste liquid circuit 5 for discharging a waste liquid from the blood purifier 3.

The blood circuit 2, the liquid supply circuits 4 (a dialysate circuit 6 and a replenishing liquid circuit 7 described later) and the waste liquid circuit 5 are composed of flexible tubes, and it is configured that plural types of tubes with different inner diameters (priming volumes) are applicable thereto. Tubes used for each circuit are basically in a set, and in the used state, tubes of all circuits are of the same type (the same inner diameter and the same priming volume).

An artery-side puncture needle 21 is provided at one end of the blood circuit 2, and a vein-side puncture needle 22 is provided at the other end. In addition, a first air bubble detector 23, a blood pump 24, the blood purifier 3, a gas-liquid separator 25 and a second air bubble detector 26 are sequentially provided on the blood circuit 2 from the artery-side puncture needle 21-side toward the vein-side puncture needle 22-side. The first air bubble detector 23 and the second air bubble detector 26 each have an air bubble detection sensor for detecting air bubbles and a mechanism for clamping (gripping and blocking) the blood circuit 2 when air bubbles are detected.

The blood pump 24 is composed of a peristaltic pump that squeezes the tube to cause blood to flow toward the blood purifier 3. The blood purifier 3 is a device also called a dialyzer and purifies the blood by bringing the blood into contact with a dialysate through a blood purification membrane (not shown). The gas-liquid separator 25 is configured to remove air bubbles and allows passage of only liquid toward the vein-side puncture needle 22-side.

In the present embodiment, the blood purification device 1 has two circuits, the dialysate circuit 6 for supplying a dialysate and the replenishing liquid circuit 7 for supplying a replenishing liquid, as the liquid supply circuits 4 so as to be able to perform various treatments. In this regard, however, the blood purification device 1 may have only one of the dialysate circuit 6 and the replenishing liquid circuit 7.

A dialysate storage bag 61 holding the dialysate is connected to one end of the dialysate circuit 6. The other end of the dialysate circuit 6 is connected to a dialysate introduction port of the blood purifier 3. A dialysate transfer pump 62, a dialysate subdivision chamber 63 for temporarily storing the dialysate, a dialysate pump 64, and a dialysate heater 65 are sequentially provided on the dialysate circuit 6 from the dialysate storage bag 61-side toward the blood purifier 3-side. The dialysate subdivision chamber 63 is one aspect of the supply liquid subdivision chamber of the invention.

The dialysate transfer pump 62 and the dialysate pump 64 are each composed of a peristaltic pump that squeezes the tube to cause the dialysate to flow. The dialysate transfer pump 62 is used to transfer the dialysate in the dialysate storage bag 61 to the dialysate subdivision chamber 63. The dialysate pump 64 is used to cause the dialysate in the dialysate subdivision chamber 63 to flow toward the blood purifier 3. Having the dialysate subdivision chamber 63 allows the dialysate storage bag 61 to be replaced without interrupting the treatment. The dialysate heater 65 is to heat the dialysate to an appropriate temperature so that the temperature of the blood to be returned to the patient is not lowered.

A replenishing liquid storage bag 71 holding the replenishing liquid is connected to one end of the replenishing liquid circuit 7. A replenishing liquid transfer pump 72, a replenishing liquid subdivision chamber 73 for temporarily storing the replenishing liquid, a replacement pump 74, a replenishing liquid heater 75 and a gas-liquid separator 76 for replenishing liquid are sequentially provided on the replenishing liquid circuit 7 on the downstream side of the replenishing liquid storage bag 71. The replenishing liquid subdivision chamber 73 is one aspect of the supply liquid subdivision chamber of the invention.

In addition, the replenishing liquid circuit 7 branches off on the downstream side of the gas-liquid separator 76 for replenishing liquid, and an end of a pre-fluid replacement circuit 7a as one of the branches of the replenishing liquid circuit 7 is connected to the blood circuit 2 between the blood purifier 3 and the blood pump 24. A pre-fluid replacement pump 77 is provided on the pre-fluid replacement circuit 7a. An end of a post-fluid replacement circuit 7b as the other branch of the replenishing liquid circuit 7 is connected to the gas-liquid separator 25 on the blood circuit 2.

The replenishing liquid transfer pump 72, the replacement pump 74 and the pre-fluid replacement pump 77 are each composed of a peristaltic pump that squeezes the tube to cause the replenishing liquid to flow. The replenishing liquid transfer pump 72 is used to transfer the replenishing liquid in the replenishing liquid storage bag 71 to the replenishing liquid subdivision chamber 73. The replacement pump 74 is used to cause the replenishing liquid in the replenishing liquid subdivision chamber 73 to flow toward the blood circuit 2. The pre-fluid replacement pump 77 is activated when performing "pre-fluid replacement" to supply the replenishing liquid to the blood circuit 2 on the upstream side of the blood purifier 3. When the pre-fluid replacement pump 77 is not activated, the replenishing liquid pumped out by the replacement pump 74 passes through the post-fluid replacement circuit 7b, and "post-fluid replacement" for supplying the replenishing liquid to the blood circuit 2 on the downstream side of the blood purifier 3 (to the gas-liquid separator 25 in this example) is performed.

Having the replenishing liquid subdivision chamber 73 allows the replenishing liquid storage bag 71 to be replaced without interrupting the treatment. The replenishing liquid heater 75 is to heat the replenishing liquid to an appropriate temperature so that the temperature of the blood to be returned to the patient is not lowered. The gas-liquid separator 76 for replenishing liquid is to separate and remove air bubbles from the replenishing liquid.

One end of the waste liquid circuit 5 is connected to a waste liquid outlet of the blood purifier 3. A waste liquid pump 51, a waste liquid subdivision chamber 52 for temporarily storing the waste liquid and a discharge pump 53 are sequentially provided on the waste liquid circuit 5 on the downstream side of the blood purifier 3. The other end of the waste liquid circuit 5 is a waste liquid outlet 54 for discharging the waste liquid to the outside of the device.

The waste liquid pump 51 and the discharge pump 53 are each composed of a peristaltic pump that squeezes the tube to cause the waste liquid to flow. The waste liquid pump 51 is used to send the waste liquid to the waste liquid subdivision chamber 52. The discharge pump 53 is used to discharge the waste liquid in the waste liquid subdivision chamber 52 toward the waste liquid outlet 54.

The blood purification device 1 also has a removed water amount detection unit 10 that detects an amount of removed water as a water balance amount of the supply liquid and the waste liquid. The removed water amount detection unit 10 has the respective subdivision chambers 63, 73, 52, a load meter 8 as a weight detection mechanism capable of detecting a total weight of the respective subdivision chambers 63, 73, 52, and a change amount calculation unit 91. The amount of removed water here is a water balance amount when the water balance amount of the supply liquid and the waste liquid is negative. In the following description, the case where the water balance amount is negative will be described, and the water balance amount is described as the amount of removed water. However, the invention is also applicable when the water balance amount of the supply liquid and the waste liquid is positive (e.g., when performing fluid replacement).

The load meter 8 is configured to be able to detect a total weight of the dialysate subdivision chamber 63, the replenishing liquid subdivision chamber 73 and the waste liquid subdivision chamber 52. A detection value of the load meter 8 is output to a control device 9.

When the amount of removed water is, e.g., 0 (zero), the supplied amount of the dialysate or the replenishing liquid is equal to the discharged amount of the waste liquid. Therefore, the reduced amount of the dialysate or the replenishing liquid in the subdivision chamber 63 or 73 is equal to the increased amount of the waste liquid in the waste liquid subdivision chamber 52 and the detection value of the load meter 8 does not change temporally. On the other hand, when the amount of removed water is large, the increased amount of the waste liquid in the waste liquid subdivision chamber 52 becomes greater than the reduced amount of the dialysate or the replenishing liquid in the subdivision chamber 63 or 73. Thus, the detection value of the load meter 8 gradually increases. Therefore, it is possible to detect the amount of removed water by detecting a temporal change in the detection value of the load meter 8 (an amount of change in weight).

In the present embodiment, the temporal change in the detection value of the load meter 8, i.e., the amount of change in weight detected by the weight detection mechanism (the amount of change in weight per unit time, i.e., slope) is used as an index of the amount of removed water. Time to measure the load when calculating the amount of change in weight is referred to as detection time. The change amount calculation unit 91 calculates the amount of change in weight in the set detection time. The change amount calculation unit 91 is mounted on the control device 9 and is realized by appropriately combining an arithmetic element such as CPU, a memory, a storage device, a software, and an interface, etc.

The change amount calculation unit 91 preferably uses load data measured by the load meter 8 at every predetermined time interval being set to shorter than the set detection time (time for the removed water amount detection unit 10 to detect the amount of removed water) and calculates the amount of change in (slope of) weight in the detection time by the method of least squares. As a result, it is possible to suppress variation in the load detection value due to pulsation of each pump, allowing for pump speed (pump flow rate) correction with higher accuracy.

The blood purification device 1 repeats a measurement preparation phase in which the dialysate or the replenishing liquid in the storage bag 61 or 71 is transferred to the subdivision chamber 63 or 73 by the transfer pump 62 or 72 and the waste liquid in the waste liquid subdivision chamber 52 is discharged by the discharge pump 53, and a measurement phase in which the transfer pump 62 or 72 and the discharge pump 53 are stopped and measurement by the load meter 8 is conducted to determine the amount of change in weight. By changing the amount of the dialysate or the replenishing liquid transferred to the subdivision chamber 63 or 73 in the measurement preparation phase, it is possible to appropriately change duration of the measurement phase, i.e., the detection time described above. When, e.g., long detection time is desired, the amount of the dialysate or the replenishing liquid transferred to the subdivision chamber 63 or 73 in the measurement preparation phase is increased. In this regard, each pump (the blood pump 24, the dialysate transfer pump 62, the dialysate pump 64, the replenishing liquid transfer pump 72, the replacement pump 74, the pre-fluid replacement pump 77, the waste liquid pump 51 and the discharge pump 53) is controlled by the control device 9.

The blood purification device 1 also includes a removed water amount control unit 92 that corrects the pump speed (the pump flow rate) of one or both of the liquid supply pump (the dialysate pump 64 or the replacement pump 74)

and the waste liquid pump 51 so that the amount of removed water detected by the removed water amount detection unit 10 matches a target removed water amount. In the present embodiment, the removed water amount control unit 92 is configured to correct the pump speed so that the amount of change in (slope of) weight calculated by the change amount calculation unit 91 matches a target value of the amount of change in (slope of) weight resulting in the target removed water amount. The removed water amount control unit 92 uses feedback control such as PID control and PI control so as to be able to promptly control the amount of removed water so that the amount of change in (slope of) weight becomes close to the target value. The removed water amount control unit 92 is mounted on the control device 9 and is realized by appropriately combining an arithmetic element such as CPU, a memory, a storage device, a software, and an interface, etc.

The pump speeds of the liquid supply pump (the dialysate pump 64 or the replacement pump 74) and the waste liquid outlet 54 may be both corrected, but the control is complicated. Therefore, it is more desirable that the pump speed of one of them be corrected while maintaining the pump speed of the other constant. In addition, when using both the dialysate pump 64 and the replacement pump 74 (when simultaneously performing dialysis treatment and fluid replacement treatment), it should be configured to correct the pump speed of the waste liquid pump 51 to further simplify the control.

Tube Identification Process

The blood purification device 1 in the present embodiment includes a tube identification unit 11 that performs a tube identification process for identifying a tube used for the blood circuit 2, the liquid supply circuit 4 or the waste liquid circuit 5, based on an amount of liquid sent from a peristaltic pump provided on the blood circuit 2, the liquid supply circuit 4 or the waste liquid circuit 5, or pressure fluctuation in the circuit, caused when driving the pump for a predetermined time. In the present embodiment, the tube identification unit 11 identifies whether a standard PV circuit tube is used or a low PV circuit tube is used. That is, the tube identification unit 11 identifies an inner diameter (or a cross-sectional area of a flow path or a priming volume) of the tube used for each circuit. Here, the standard PV circuit is a blood purification circuit (the blood circuit 2, the liquid supply circuit 4, the waste liquid circuit 5) with standard priming volume and the low PV circuit is a blood purification circuit (the blood circuit 2, the liquid supply circuit 4, the waste liquid circuit 5) with low priming volume. Although the tube identification unit 11 in the present embodiment identifies whether the standard PV circuit tube is used or the low PV circuit tube is used, it is not limited thereto as long as the tube identification unit 11 can identify for which circuit the tube is used in case that plural circuits with different priming volumes can be used.

In the present embodiment, the tube identification unit 11 has an identification unit 93 that detects the amount of liquid sent from the pump when the pump provided on the liquid supply circuit 4 or the waste liquid circuit 5 is driven for a predetermined time, based on the detection result of the weight detection mechanism of the removed water amount detection unit 10, i.e., the load meter 8. The identification unit 93 is mounted on the control device 9 and is realized by appropriately combining an arithmetic element such as CPU, a memory, a storage device, a software, and an interface, etc.

In the present embodiment, any of the dialysate transfer pump 62, the dialysate pump 64, the replenishing liquid transfer pump 72, the replacement pump 74, the waste liquid pump 51 or the discharge pump 53 can be used as the pump driven at the time of tube identification. Since the pump speed (the pump flow rate) can be corrected using the amount of liquid sent from the pump that is measured during the tube identification process in the present embodiment (the details will be described later), the pump driven during the tube identification process is more desirably the dialysate pump 64, the replacement pump 74 or the waste liquid pump 51 from which more accurate pump speeds (pump flow rates) can be obtained. Hereinafter, the case where the dialysate pump 64 is driven during the tube identification process will be described as an example. During the tube identification process, the other pumps should be stopped so as not to affect the detection result of the load meter 8.

In the present embodiment, the load meter 8 provided for detecting the amount of removed water is used to detect the amount of liquid sent from the pump, as described above. Therefore, the tube identification process can be achieved at low cost and can be easily applied to existing devices having the load meter 8. However, the means for detecting the amount of liquid sent from the pump when driving the pump during the tube identification process is not limited thereto and, e.g., a flow meter, etc., may be used.

The identification unit 93 drives the dialysate pump 64 for a predetermined time (a predetermined number of revolutions), and detects an amount of change in a load detected by the load meter 8 before and after the drive. When this amount of change in the load is within a preset standard PV threshold range, the identification unit 93 determines that the standard PV circuit tube is used for each circuit. Likewise, when the amount of change in the load detected by the load meter is within a preset low PV threshold range, the identification unit 93 determines that the low PV circuit tube is used for each circuit. The standard PV threshold range and the low PV threshold range are set to appropriate numerical ranges, taking into consideration the manufacturing tolerances of the tube or treatment conditions.

In addition, in the present embodiment, the identification unit 93 is configured so as to be able to determine whether or not there is an abnormality in the tube in use, based on whether or not the amount of change in the load detected by the load meter falls within a preset normal range. In more particular, the identification unit 93 determines that there is an abnormality in the tube when the amount of change in the load detected by the load meter does not fall within the standard PV threshold range and the low PV threshold range described above.

Since it is difficult to replace the tube of each circuit after beginning the treatment, it is desirable to the perform tube identification process before beginning the treatment. In the present embodiment, the identification unit 93 is configured to perform the tube identification process when priming each circuit with a liquid such as physiological saline solution or dialysate (e.g., when introducing a liquid into each circuit) before blood purification treatment. That is, the pump driven during the tube identification process discharges a physiological saline solution for priming, and the tube used for each circuit is identified by detecting the amount of the sent physiological saline solution.

It is also possible to identify the tube in use by using the blood pump 24 provided on the blood circuit 2. In this case, the flow rate when driving the blood pump 24 for a predetermined time may be obtained using a flow rate sensor for measuring the amount of liquid sent (discharged) from of the blood pump 24. It is also possible to estimate the flow rate of the blood pump 24 by, e.g., driving the blood pump 24 for a predetermined time in a state that the blood circuit 2 is clamped (blocked) at the first air bubble detector 23, and then measuring the pressure fluctuation on the inlet side of the blood pump 24 (on the first air bubble detector 23 side) using a pressure sensor.

The blood purification device 1 also includes an alarm unit 12 that issues an alarm when the type of the tube actually used for each circuit and identified by the tube identification unit 11 (the identification unit 93) does not match the type of tube of each circuit in a preset setting and also when the tube identification unit 11 (the identification unit 93) detects an abnormality in the tube.

The alarm unit 12 has an alarm device 94a for issuing an alarm by light, sound or vibration, etc., and an alarm control unit 94 for controlling the alarm device 94a. The alarm device 94a is composed of, e.g., a buzzer emitting a warning tone by sound, or a mechanism for producing solid or blinking warning light, etc. The alarm control unit 94 is mounted on the control device 9 and is realized by appropriately combining an arithmetic element such as CPU, a memory, a storage device, a software, and an interface, etc.

In the present embodiment, the blood purification device 1 includes a display 100 for displaying a predetermined screen showing an operation guide, the device status, and the treatment status, etc. Then, the alarm control unit 94 of the alarm unit 12 is configured to issue an alarm by displaying an alarm screen 101 corresponding to the details of the alarm on the display 100, as shown in FIGS. 2A, 2B and 2C.

Figure 2A:
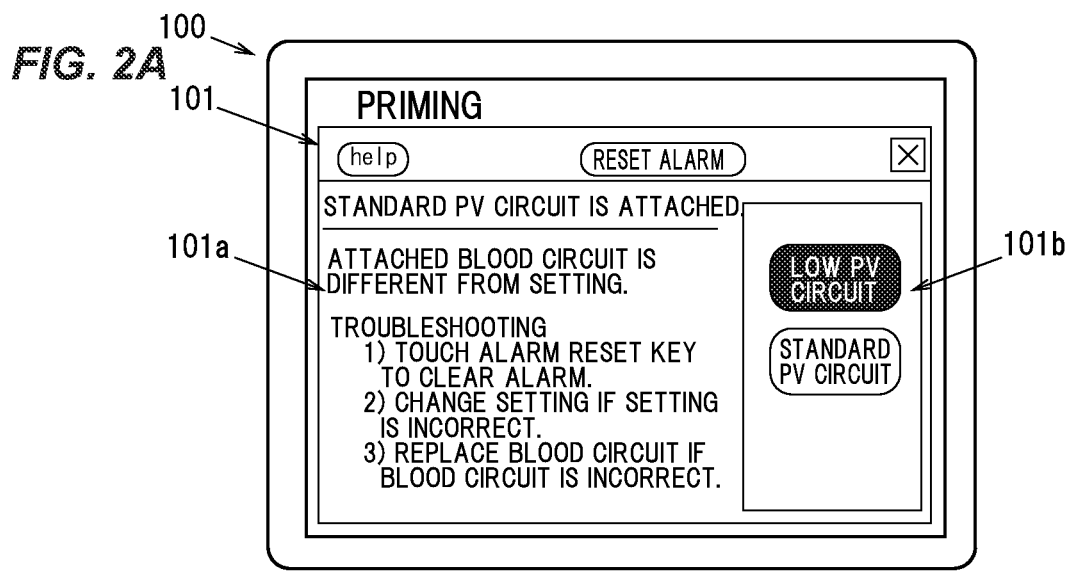
FIG. 2A is a diagram illustrating an example display shown on an alarm screen when a tube in the setting does not match a tube in use.
Figure 2B:
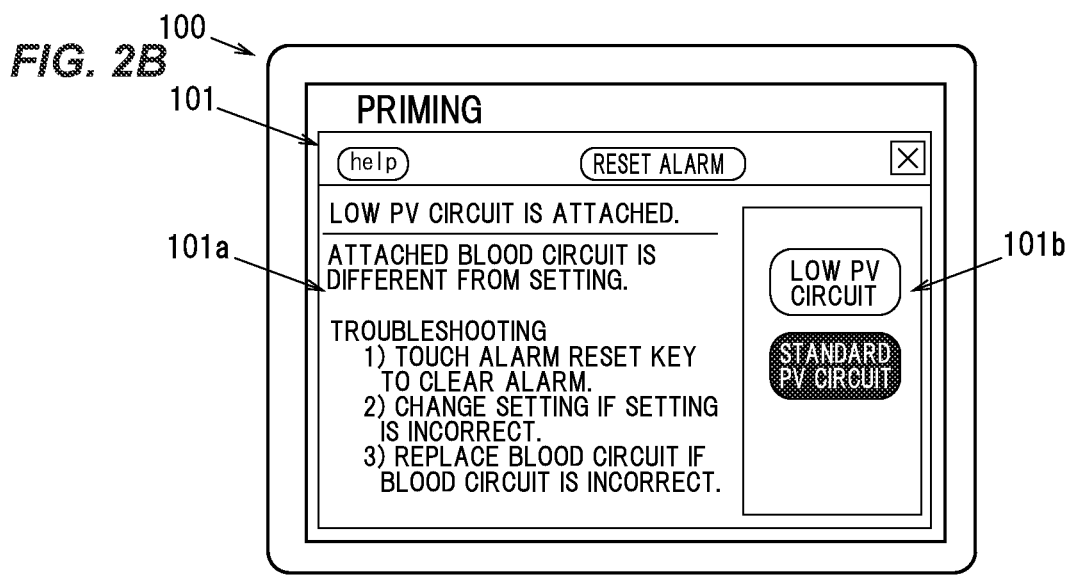
FIG. 2B is a diagram illustrating an example display shown on the alarm screen when the tube in the setting does not match the tube in use.

When, e.g., the standard PV circuit tube is attached even though the setting is for the low PV circuit, messages or how to troubleshoot such as "Standard PV circuit is attached" and "Attached circuit is different from the setting" are displayed on a message part 101a of the alarm screen 101, as shown in FIG. 2A. Meanwhile, when, e.g., the low PV circuit tube is attached even though the setting is for the standard PV circuit, messages or how to troubleshoot such as "Low PV circuit is attached" and "Attached circuit is different from the setting" are displayed on the message part 101a of the alarm screen 101, as shown in FIG. 2B.

In the present embodiment, a setting change reception part 101b for receiving an operation to change a preset tube setting is displayed on the alarm screen 101. That is, in the present embodiment, when the tube in the setting is different from the attached tube, the setting can be changed on the setting change reception part 101b of the alarm screen 101. Since this eliminates the necessity of inputting the setting details all over again, convenience is improved. In the present embodiment, a touch panel display is used as the display 100 so that an input for changing the tube setting can be performed by a touch operation. However, the input device is not specifically limited and an input may be performed by hard keys.

Figure 2C:
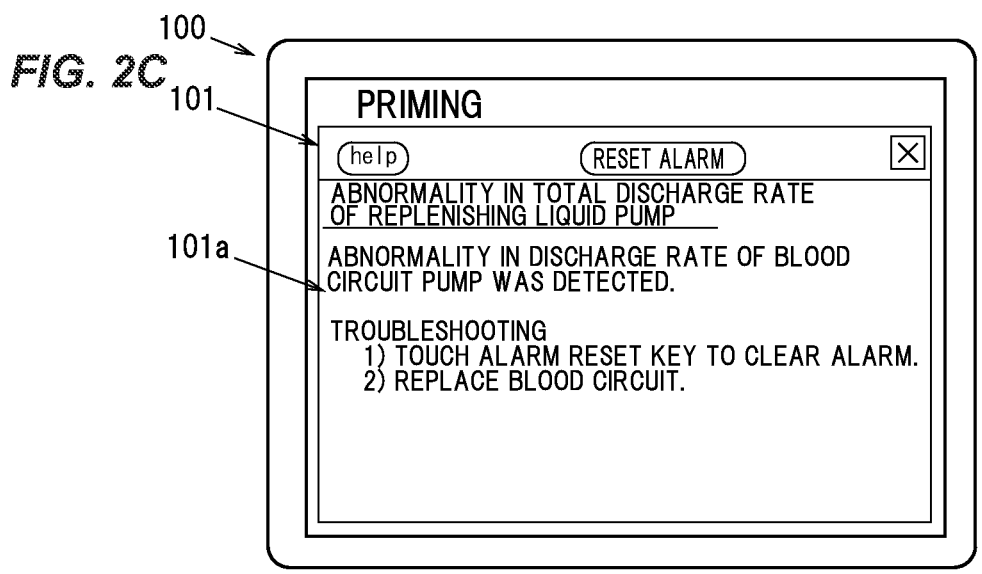
FIG. 2C is a diagram illustrating an example display shown on the alarm screen when determined that the there is an abnormality in the tube.

When an abnormality in the tube is detected, messages or how to troubleshoot such as "Abnormality in total discharge rate of replacement pump" and "Abnormality in discharge rate of blood circuit pump was detected" are displayed on the message part 101a of the alarm screen 101, as shown in FIG. 2C.

The blood purification device 1 further includes a pump speed correction unit 95 that corrects the pump speed of the pump (in this example, the dialysate pump 64) driven at the time of the measurement, based on a measurement result of the pump flow rate of the pump or the pressure fluctuation in the circuit before and after the pump (in this example, the amount of change in load before and after driving the pump) during the tube identification process. The pump speeds (the pump flow rates) of the dialysate pump 64, etc., are corrected by the removed water amount control unit 92 after beginning the treatment as described above, but having the pump speed correction unit 95 can further reduce an error of the amount of removed water and suppress waste of expensive dialysate or replenishing liquid since the pump speed is corrected at the time of beginning the treatment. The pump speed correction unit 95 is mounted on the control device 9 and is realized by appropriately combining an arithmetic element such as CPU, a memory, a storage device, a software, and an interface, etc.

Although the tube identification process in the present embodiment is performed by driving only the dialysate pump 64, the tube identification process may be performed using plural pumps. For example, by performing the tube identification process using the dialysate pump 64, the replacement pump 74 and the waste liquid pump 51, it is possible to detect whether or not there is an abnormality in each of the dialysate pump 64, the replacement pump 74 and the waste liquid pump 51, and it is also possible to begin the treatment in a state that the pump speeds (the pump flow rates) of the respective pumps 64, 74, and 51 have been corrected, which allows the amount of removed water to be controlled with high accuracy from the beginning of the treatment.

Figure 3:
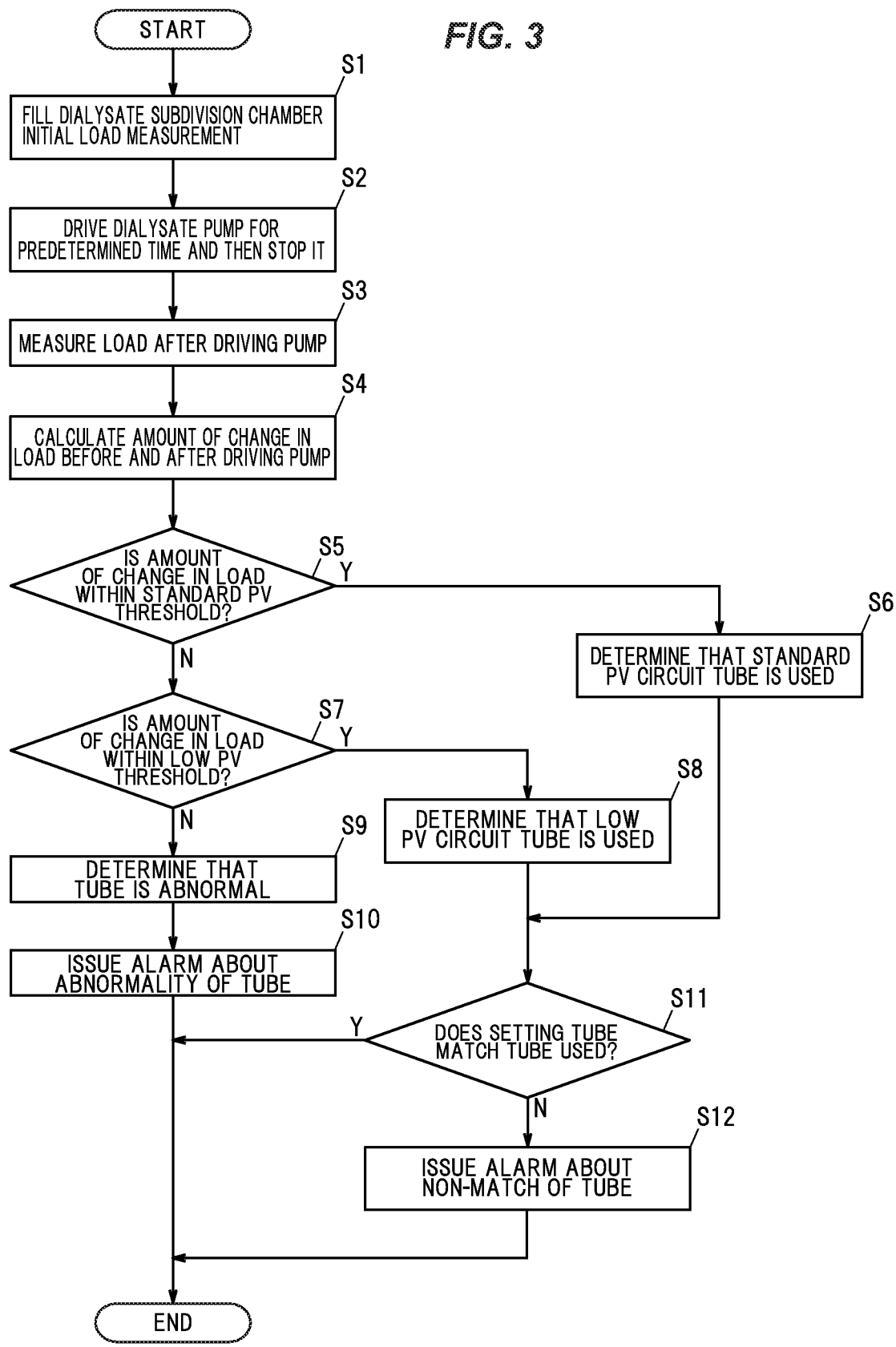
FIG. 3 is a flowchart showing a control flow of a tube identification process.

FIG. 3 is a flowchart showing a control flow of the tube identification process. The control flow of FIG. 3 is initiated when each circuit is filled with a physiological saline solution by priming.

As shown in FIG. 3, firstly, the dialysate transfer pump 62 is driven to fill the dialysate subdivision chamber 63 with a physiological saline solution, and a load at this time is measured by the load meter 8 in Step S1. After that, the dialysate pump 64 is driven for a predetermined time and is then stopped in Step S2. At this time, the pumps other than the dialysate pump 64 are stopped. Then, the load is measured by the load meter 8 in Step S3 and an amount of change from the initial load measured in Step S1 is obtained in Step S4.

After that, in Step S5, it is determined whether the amount of change in the load obtained in Step S4 is within the standard PV threshold range. When the determination made in Step 5 is Yes, it is determined that the tube in use is a standard PV circuit tube in Step S6, and the process proceeds to Step S11.

When the determination made in Step S5 is No, it is determined whether the amount of change in the load obtained in Step S4 is within the low PV threshold range in Step S7. When the determination made in Step S7 is Yes, it is determined that the tube in use is a low PV circuit tube in Step S8, and the process proceeds to Step S11. When the determination made in Step S7 is No, it is determined that there is an abnormality in the tube in Step S9, an alarm about abnormality of the tube is issued in Step S10, and the process ends.

In Step S11, it is determined whether the type of the tube in the setting matches the type of the tube in use. When the determination made in Step S1*l* is Yes, the process ends. When the determination made in Step S1*l* is No, an alarm about non-match of tube is issued in Step S12, and the process ends.

Functions and Effects of the Embodiment

As described above, the blood purification device 1 in the present embodiment includes the tube identification unit 11 that performs the tube identification process for identifying the tube used for the blood circuit 2, the liquid supply circuit 4 or the waste liquid circuit 5 or determining whether or not there is an abnormality in the tube, based on an amount of liquid sent from a peristaltic pump provided on the blood circuit 2, the liquid supply circuit 4 or the waste liquid circuit 5, or pressure fluctuation in the circuit, caused when driving the pump for a predetermined time.

By having the tube identification unit 11, it is possible to suppress use of a tube having a priming volume different from the setting and also it is possible to detect an abnormality in the tube, thereby allowing for safer treatment. As a result, a problem, in which an unintended flow rate control is performed and an intended treatment effect is not obtained, can be suppressed.

Summary of the Embodiment

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A blood purification device (1), comprising: a blood circuit (2) for extracorporeally circulating blood of a patient; a liquid supply circuit (4) for supplying a supply liquid to the blood circuit (2) or to a blood purifier (3) provided on the blood circuit (2); and a waste liquid circuit (5) for discharging a waste liquid from the blood purifier (3), wherein each of the blood circuit (2), the liquid supply circuit (4) and the waste liquid circuit (5) comprises a flexible tube, a plurality of types of tubes with different inner diameters are applicable as each circuit, and the device (1) comprises a tube identification unit (11) that performs a tube identification process for identifying a tube used for the blood circuit (2), the liquid supply circuit (4) or the waste liquid circuit (5) or determining whether or not there is an abnormality in the tube, based on an amount of liquid sent from a peristaltic pump provided on the blood circuit (2), the liquid supply circuit (4) or the waste liquid circuit (5), or pressure fluctuation in the circuit, caused when driving the pump for a predetermined time.

[2] The blood purification device (1) described in [1], comprising: a removed water amount detection unit (10) for detecting an amount of removed water based on a supplied amount of the supply liquid and a discharged amount of the waste liquid, wherein the removed water amount detection unit comprises a supply liquid subdivision chamber (63, 73) being provided on the liquid supply circuit (4) and temporarily storing the supply liquid, a waste liquid subdivision chamber (52) being provided on the waste liquid circuit (5) and temporarily storing the waste liquid, and a weight detection mechanism (8) for detecting a total weight of the supply liquid subdivision chamber (63, 73) and the waste liquid subdivision chamber (5), and the tube identification unit (11) uses the weight detection mechanism (8) of the removed water amount detection unit (10) and detects the amount of liquid sent from the pump when driving the pump provided on the liquid supply circuit (4) or the waste liquid circuit (5) for a predetermined time.

[3] The blood purification device (1) described in [1] or [2], wherein the tube identification unit (11) performs the tube identification process during when priming each circuit with a liquid before blood purification treatment.

[4] The blood purification device (1) described in any one of [1] to [3], comprising: an alarm unit (12) that issues an alarm when the tube actually used for each circuit and identified by the tube identification unit (11) does not match a tube of each circuit in a preset setting.

[5] The blood purification device (1) described in [4], comprising: a display (100) for displaying a predetermined screen, wherein the alarm unit (12) issues an alarm by displaying an alarm screen (101) corresponding to the details of the alarm on the display (100).

[6] The blood purification device (1) described in [5], wherein a setting change reception part (101*b*) for receiving an operation to change a preset tube setting is displayed on the alarm screen (101).

[7] The blood purification device (1) described in any one of [1] to [6], wherein the tube identification unit (11) determines whether or not there is an abnormality in the tube in use, based on whether or not the amount of liquid sent from the pump or the pressure fluctuation when driving the pump for a predetermined time falls within a preset normal range.

[8] The blood purification device (1) described in any one of [1] to [7], comprising: a pump speed correction unit (95) that corrects a pump speed of the pump driven at the time of the measurement, based on a measurement result of the amount of liquid sent from the pump or the pressure fluctuation during the tube identification process.

Although the embodiment of the invention has been described, the invention according to claims is not to be limited the embodiment described above. In addition, all combinations of the features described in the embodiment are not necessary to solve the problem of the invention.

The invention can be appropriately modified and implemented without departing from the gist thereof. For example, although a tube having a circular cross-sectional shape is used for each circuit in the embodiment described above, it is not limited thereto. The cross-sectional shape may be, e.g., an elliptical shape, a rounded square shape, or a polygonal shape.

REFERENCE SIGNS LIST

1: blood purification device
2: blood circuit
24: blood pump
3: blood purifier
4: liquid supply circuit
5: waste liquid circuit
51: waste liquid pump
52: waste liquid subdivision chamber
53: discharge pump
6: dialysate circuit
62: dialysate transfer pump
63: dialysate subdivision chamber (supply liquid subdivision chamber)
64: dialysate pump
7: replenishing liquid circuit
72: replenishing liquid transfer pump
73: replenishing liquid subdivision chamber (supply liquid subdivision chamber)
74: replacement pump
8: load meter (weight detection mechanism)
9: control device
91: change amount calculation unit
92: removed water amount control unit
92: removed water amount control unit
93: identification unit
94: alarm control unit
94*a*: alarm device 95: pump speed correction unit
10: removed water amount detection unit
11: tube identification unit
12: alarm unit

The invention claimed is:
1. A blood purification device, comprising:
a blood circuit for extracorporeally circulating blood of a patient;
a liquid supply circuit for supplying a supply liquid to the blood circuit or to a blood purifier provided on the blood circuit;
a waste liquid circuit for discharging the waste liquid from the blood purifier, and
a removed water amount detection unit for detecting an amount of removed water based on a supplied amount of the supply liquid and a discharged amount of the waste liquid;
wherein each of the blood circuit, the liquid supply circuit and the waste liquid circuit comprises a flexible tube, and the device comprises a tube identification unit that performs a tube identification process for identifying a tube used for the blood circuit, the liquid supply circuit or the waste liquid circuit or determining whether or not there is an abnormality in the tube, based on an amount of liquid sent from a peristaltic pump provided on the blood circuit, the liquid supply circuit or the waste liquid circuit, or pressure fluctuation in the circuit, caused when driving the pump for a predetermined time; and
wherein the removed water amount detection unit comprises a supply liquid subdivision chamber being provided on the liquid supply circuit and temporarily storing the supply liquid, a waste liquid subdivision chamber being provided on the waste liquid circuit and temporarily storing the waste liquid, and a weight detection mechanism for detecting a total weight of the supply liquid subdivision chamber and the waste liquid subdivision chamber, and the tube identification unit uses the weight detection mechanism of the removed water amount detection unit and detects the amount of liquid sent from the pump provided on the liquid supply circuit or the waste liquid circuit when driving the pump for a predetermined time.

2. The blood purification device according to claim 1, wherein the tube identification unit performs the tube identification process during when priming each circuit with a liquid before blood purification treatment.

3. The blood purification device according to claim 1, comprising:
an alarm unit that issues an alarm when a tube actually used for each circuit and identified by the tube identification unit does not match a tube of each circuit in a preset setting.

4. The blood purification device according to claim 3, comprising:
a display for displaying a predetermined screen,
wherein the alarm unit issues an alarm by displaying an alarm screen corresponding to the details of the alarm on the display.

5. The blood purification device according to claim 4, wherein a setting change reception part for receiving an operation to change a preset tube setting is displayed on the alarm screen.

6. A blood purification device, comprising:
a blood circuit for extracorporeally circulating blood of a patient
a liquid supply circuit for supplying a supply liquid to the blood circuit or to a blood purifier provided on the blood circuit and
a waste liquid circuit for discharging the waste liquid from the blood purifier,
wherein each of the blood circuit, the liquid supply circuit and the waste liquid circuit comprises a flexible tube, and the device comprises a tube identification unit that performs a tube identification process for identifying a tube used for the blood circuit, the liquid supply circuit or the waste liquid circuit or determining whether or not there is an abnormality in the tube, based on an amount of liquid sent from a peristaltic pump provided on the blood circuit, the liquid supply circuit or the waste liquid circuit, or pressure fluctuation in the circuit, caused when driving the pump for a predetermined time; and
wherein the tube identification unit determines whether or not there is an abnormality in the tube in use, based on whether or not the amount of liquid sent from the pump or the pressure fluctuation when driving the pump for a predetermined time falls within a preset normal range.

7. The blood purification device according to claim 1, comprising:
a removed water amount detection unit for detecting an amount of removed water based on a supplied amount of the supply liquid and a discharged amount of the waste liquid,
wherein the removed water amount detection unit comprises a supply liquid subdivision chamber being provided on the liquid supply circuit and temporarily storing the supply liquid, a waste liquid subdivision chamber being provided on the waste liquid circuit and temporarily storing the waste liquid, and a weight detection mechanism for detecting a total weight of the supply liquid subdivision chamber and the waste liquid subdivision chamber, and the tube identification unit uses the weight detection mechanism of the removed water amount detection unit and detects the amount of liquid sent from the pump provided on the liquid supply circuit or the waste liquid circuit when driving the pump for a predetermined time.

8. A blood purification device, comprising:
a blood circuit for extracorporeally circulating blood of a patient
a liquid supply circuit for supplying a supply liquid to the blood circuit or to a blood purifier provided on the blood circuit and
a waste liquid circuit for discharging the waste liquid from the blood purifier,
wherein each of the blood circuit, the liquid supply circuit and the waste liquid circuit comprises a flexible tube, and the device comprises a tube identification unit that performs a tube identification process for identifying a tube used for the blood circuit, the liquid supply circuit or the waste liquid circuit or determining whether or not there is an abnormality in the tube, based on an amount of liquid sent from a peristaltic pump provided on the blood circuit, the liquid supply circuit or the waste liquid circuit, or pressure fluctuation in the circuit, caused when driving the pump for a predetermined time; and
a pump speed correction unit that corrects a pump speed of the pump driven at the time of the measurement, based on a measurement result of the amount of liquid sent from the pump or the pressure fluctuation during the tube identification process.

* * * * *